United States Patent [19]
Zygmont

[11] Patent Number: 5,919,152
[45] Date of Patent: Jul. 6, 1999

[54] ANTIBACTERIAL SWABS

[75] Inventor: Joseph Frank Zygmont, Killingworth, Conn.

[73] Assignee: Chesebrough-Pond's USA Co., Division of Conopco, Inc., Greenwich, Conn.

[21] Appl. No.: 09/140,252

[22] Filed: Aug. 26, 1998

Related U.S. Application Data

[63] Continuation-in-part of application No. 08/989,072, Dec. 11, 1997, Pat. No. 5,846,215.
[51] Int. Cl.$^6$ .................................................. A61M 35/00
[52] U.S. Cl. ..................................................... 604/1
[58] Field of Search ............................................ 604/1–3

[56] References Cited

U.S. PATENT DOCUMENTS

| | | |
|---|---|---|
| 1,822,567 | 9/1931 | Davies . |
| 3,090,080 | 5/1963 | Pellicone et al. . |
| 3,343,540 | 9/1967 | Siegel . |
| 3,452,650 | 7/1969 | Cobb . |
| 4,887,994 | 12/1989 | Bedford . |
| 5,676,643 | 10/1997 | Cann et al. . |
| 5,704,906 | 1/1998 | Fox . |

FOREIGN PATENT DOCUMENTS 200647  5/1974  Canada .

*Primary Examiner*—John G. Weiss
*Assistant Examiner*—Dennis Ruhl
*Attorney, Agent, or Firm*—Milton L. Honig

[57] ABSTRACT

A swab is provided which includes an elongate stem and an absorbent covering such as cotton surrounding opposite tips of the stem. An antimicrobial agent is dispersed within the absorbent covering. A process is also provided for manufacturing the swabs. The process includes the steps of preparing a liquid medium containing the antimicrobial agent, contacting the absorbent covering with the liquid medium and then drying the absorbent covering.

7 Claims, 1 Drawing Sheet

ANTIBACTERIAL SWABS

This is a continuation-in-part of Ser. No. 08/989,072, filed Dec. 11, 1997 now U.S. Pat. No. 5,846,215.

BACKGROUND OF THE INVENTION

1. Field of the Invention

The invention concerns cotton swabs having resistance to bacterial contamination.

2. The Related Art

Swabs articles having an elongated stem and an absorbent covering on the tips are well known. Cotton is generally used as the absorbent covering. Stems are constituted of wood, rolled paper or plastic.

Most often the swabs are used for personal hygiene. They are particularly functional for cleaning the outer surfaces of the ear and even for applying cosmetics to the face and other parts of the body.

Airborne bacteria are especially prevalent in bathrooms and medical offices/hospitals. Coincidentally swabs are usually housed and employed in these areas. Thus the risks of swabs becoming contaminated is greatly increased. It would therefore be highly desirable to ensure that the cotton tips be protected against microbial contamination.

U.S. Pat. No. 4,887,994 (Bedford) discloses an applicator saturated with a disinfecting liquid. The product is sealed within a liquid-impervious pouch. The intent of this product is to deliver disinfecting liquids to wounds.

A similar concept is disclosed in U.S. Pat. No. 3,343,540 (Siegel) which seeks to transfer a medicament, which may be an anti-infective or antibacterial agent, to a portion of the human body. This approach is somewhat different from the Bedford patent in that the active agents are held on the applicator in a dried state. An encapsulating water-soluble resin surrounds the actives. The encapsulates are deposited onto the absorbent coverings (e.g. cotton) of the applicators. Release of the actives occurs when the applicator tip is wetted with water. The water soluble resin dissolves releasing the anti-infective or antibacterial agent. Nothing is mentioned with respect to protecting the swab itself from contamination. Indeed, encapsulation separates the active from any protective interaction with the absorbent covering or applicator stick. By contrast, swab articles of the present invention exclude antibacterial agents stored in liquid form on the swab. Also excluded are antibacterial agents encapsulated within resins or waxes.

Accordingly, it is an object of the present invention to provide a swab with absorbent coverings at either end of a stem which have been reinforced against microbial contamination.

Another object of the present invention is to provide a procedure for uniformly distributing antimicrobial actives into the absorbent coverings of swab sticks.

These and other objects of the present will become more readily apparent from consideration of the following summary and detailed description.

SUMMARY OF THE INVENTION

A swab is provided which includes:

an elongate stem with first and second ends opposite one another;

an absorbent covering surrounding each of the first and second ends; and an antibacterial agent dispersed within the absorbent covering.

A process is provided for manufacturing swabs, the swabs being formed from an elongate stem with first and second ends opposite one another and an absorbent covering surrounding each of the first and second ends. The process includes the steps of:

preparing a liquid medium containing from 0.0001 to 50% by weight of an antibacterial agent;

contacting the absorbent covering with the liquid medium containing the antibacterial agent; and drying the absorbent covering which has been contacted with the antibacterial agent.

DETAILED DESCRIPTION OF THE DRAWINGS

Figure 1:
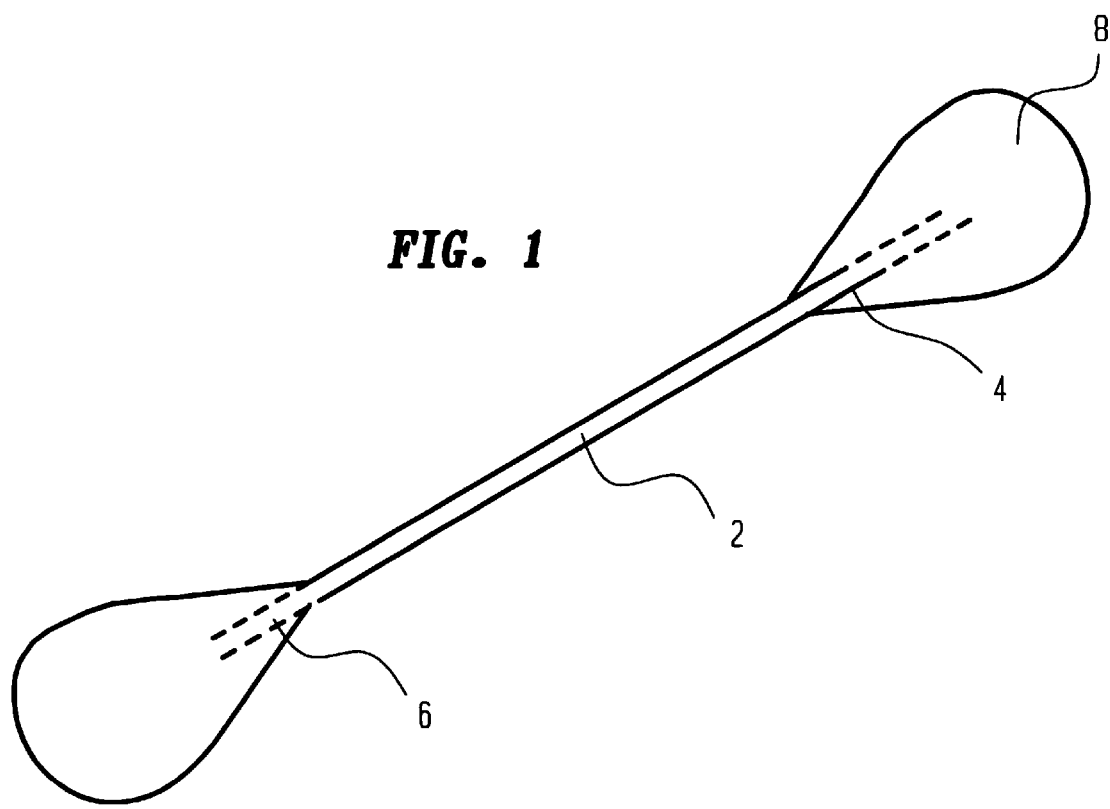
Figure 2:
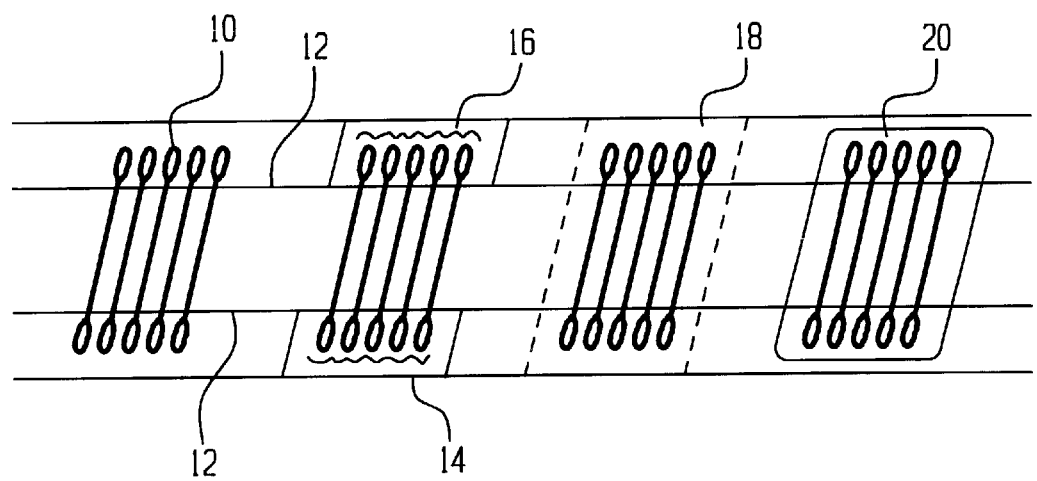

The above features, advantages and objectives of the present invention will be more fully appreciated through the following detailed discussion, reference being made to the drawing in which:

FIG. 1 is a plan perspective view of a swab according to the present invention; and FIG. 2 is a highly schematic illustration of the process for delivering antibacterial agent onto the absorbent covering of the swabs.

DETAILED DESCRIPTION

Swabs, especially cotton swabs can be rendered less susceptible to microbial contamination by impregnating antibacterial agents onto cotton or other absorbent coverings surrounding ends of the swab.

FIG. 1 illustrates a typical swab with an elongate stem 2 having first and second ends 4, 6 at opposite extremities from one another. An absorbent covering 8 surrounds each of the first and second ends. Cotton is the most preferred absorbent covering. However, synthetic or other natural materials with flexible and absorbent properties can also be used. For example, the absorbent covering could be formed of rayon fibers, polyester, polyurethane or other foamed or fibered synthetic polymers.

Stems of the present invention may be selected from wood, rolled paper or plastic. Typical plastic stems are formed from polyethylene or polypropylene. For cost reasons these may have hollow centers and their outer walls may have a ribbed configuration rendering them easier to grasp as well as for better anchoring of the absorbent covering on their tips. Of course, stems which are most preferred are formed of tightly rolled paper.

Swabs of the present invention based on paper stems are manufactured first by providing a die-cut paper. The paper is tightly rolled, optionally with adhesives spread on the paper to assist in preventing unraveling of the resultant stick. Cotton fibers are then applied to each of the ends. The paper rolling and cotton fiber application steps are well known in the art. Reference may be had to U.S. Pat. No. 3,090,080 (Pellicone et al.), U.S. Pat. No. 3,452,650 (Cobb) and Canadian Patent 990,564 (Cottrell).

The preferred manner of providing antibacterial protection to swabs is to begin with a pre-formed swab obtained in a manner such as described above. FIG. 2 illustrates the process according to the present invention. A series of swabs 10 are transported along a conveyor belt 12 and transmitted through a dispensing system 14 containing a padding medium 16. The padding medium is water with from 0.0001 to 30%, but preferably from 0.01 to 1%, optimally from 0.05 to 0.5% by weight of an antimicrobial agent dispersed therein.

When utilizing hydrophobic antibacterial agents such as 2', 4, 4'-trichloro-2-hydroxydiphenyl ether, it is useful to include a compatabilizing agent. Typical compatiblizing agents are polyhydric alcohols such as propylene glycol, ethylene glycol, polypropylene glycol, polyethylene glycol, polyoxyethylene-polyoxypropylene copolymers, glyceryl ethers and even glycerin. Amounts of the compatibilizing agent may range from 0.0001 to 50% by weight.

Advantageously the padding medium is a water slurry that further contains from 0.0001 to 20% by weight of a binder. Suitable thickeners include organically modified cellulose and acrylic latex. Among the cellulose materials are hydroxypropyl methylcellulose, hydroxypropyl cellulose, hydroxyethyl cellulose, hydroxymethyl cellulose, methyl cellulose and carboxymethyl cellulose.

Subsequent to being padded in the antimicrobial containing medium, the swabs are conveyed to a drying station 18. Thereafter the swabs are delivered to a packaging unit 20.

As used herein, the term "antibacterial agent" refers to a wide variety of substances having germicidal action, such as the halogenated salicylanilides, halogenated carbanilides, halogenated bisphenols, alkylbenzoylacrylates, quaternary ammonium compounds, thiuram sulfides, dithiocarbamates, antibiotics, halogenated diphenyl ethers, halogenated anilides of thiophene carboxylic acids, and chlorhexidines.

Among the halogenated salicylanilides there may be mentioned the following derivatives:

5-bromo-salicylanilide
4',5-dibromo-salicylanilide
3,4',5-tribromo-salicylanilide
6-chloro-salicylanilide
4'5-dichloro-salicylanilide
3,4'5-trichloro-salicylanilide
4',5-diiodo-salicylanilide
3,4',5-triiodo-salicylanilide
5-chloro-3'-trifluoromethyl-salicylanilide
5-chloro-2'-trifluoromethyl-salicylanilide
3,5-dibromo-3'-trifluoromethyl-salicylanilide
3-chloro-4-bromo-4'-trifluoromethyl-salicylanilide
2',5-dichloro-3-phenyl-salicylanilide
3',5-dichloro-4'-methyl-3-phenyl-salicylanilide
3',5-dichloro-4'-phenyl-3-phenyl-salicylanilide
3,3',5-trichloro-6'-(p-chlorophenoxy)-salicylanilide
3',5-dichloro-5'-(p-bromophenoxy)-salicylanilide
3,5-dichloro-6'-phenoxy-salicylanilide
3,5-dichloro-6'-(o-chlorophenoxy)-salicylanilide
5-chloro-6'-(o-chlorophenoxy)-salicylanilide
5-chloro-6'-beta-naphthyloxy-salicylanilide
5-chloro-6'-alpha-naphthyloxy-salicylanilide
3,3',4-trichloro-5,6'-beta-naphthyloxy-salicylalide;

Halogenated carbanilides are represented by the 3,4,4'-trichloro-carbanilide and the 3,3',4-trichloro derivatives and by 3-trifluoromethyl-4,4'-dichlorocarbanilide.

The bis-phenols are represented by the following:

2,2'-methylenebis(4-chlorophenol)
2,2'-methylenebis(4,5-dichlorophenol)
2,2'-methylenebis(3,4,6-trichlorophenol)
2,2'-thiobis(4,6-dichlorophenol)
2,2'-diketobis(4-bromophenol)
2,2'-methylenebis (4-chloro-6-isopropylphenol)
2,2'-isopropylidenebis(6-sec-butyl-4-chlorophenol)

The useful alkylbenzoyl acrylates comprise the sodium salts of alkylbenzoylacrylic acids wherein the alkyl portion has from about 5 to about 12 carbon atoms.

Examples of quaternary ammonium compounds are:
diisobutylphenoxyethoxyethyidimethylbenzylammonium chloride
N-methyl-N-(2-hydroxyethyl)-N-(2-hydroxydodecyl)-N-benzyl ammonium chloride
Cetyl trimethylammonium bromide
Stearyl trimethylammonium bromide
Oleyl dimethylethylammonium bromide
Lauryidimethylchlorethoxyethylammonium chloride
lauryidimethylbenzylammonium chloride
Alkyl ($C_8$–$C_{18}$)dimethyl(3,4-dichlorobenzyl)-ammonium chloride
Lauryl pyridinium bromide
Lauryl isoquinolinium bromide
N(lauroyloxyethylaminoformylmethyl)pyridinium chloride;

Examples of the thiocarbamates and the thiuram sulfides are:
disodium ethylene bis-dithiocarbamate (Nabam)
diammonium ethylene bis-dithiocarbamate (amabam)
Zn ethylene bis-dithiocarbamate (ziram)
Fe ethylene bis-dithiocarbamate (ferbam)
Mn ethylene bis-dithiocarbamate (manzate)
tetramethyl thiuram disulfide
tetrabenzyl thiuram disulfide
tetraethyl thiuram disulfide
tetramethyl thiuram sulfide From the viewpoint of safety and effectiveness the preferred antibacterial agents are as follows:

4',5-dibromosalicylanilide
3,4',5-tribromosalicylanilide
3,4',5-trichlorosalicylanilide
3,4,4'-trichlorocarbanilide
3-trifluoromethyl-4,4'-dichlorocarbanilide
2,2'-methylenebis(3,4,6-trichlorophenol)
2,4,4'-trichloro-2,'- hydroxydiphenyl ether
Tyrothricin
N-methyl-N-(2-hydroxyethyl-N-(2-hydroxydodecyl)-N-benzylammonium chloride Especially preferred are:
2,3'5-tribromosalicylanilide
chlorohexidine digluconate
chlorohexidine diaceate
4',5-dibromosalicylanilide
3,4,4'-trichlorocarbanilide
2,4,4'-trichloro-2-hydroxydiphenyl ether The following example will more fully illustrate the embodiments of this invention. All parts, percentages and proportions referred to herein and in the appended claims are by weight unless otherwise indicated.

EXAMPLE

Antibacterial efficacy of swabs according to the present invention were evaluated in a manner described below.

Test Method

Test microorganisms and media were prepared in the following manner. One tube of FDA broth culture was inoculated with a microorganism and incubated at 37° C. for 20–24 hours. Microorganisms suitable for this type culture were *S. aureus, S. epidermidis, P. vulgaris, E. coli, P. aeruginosa* and *B. subtiltis*. From the 20–24 hour culture is taken 1 ml of a 1:100 dilution in saline which is added to a 200 ml of melted Extract-FDA agar previously cooled to approximately 45° C.

For the microorganism *C. albicans*. The inoculation medium is Mycophil broth incubated for 20–24 hours at 37° C. Similar to the procedure with the other strains, a 1 ml of a 20–24 hour culture is added to 200 ml of melted Mycophil agar which has been cooled to approximately 45° C.

To each of 3 plates per sample, plus one control plate, there is added 15 ml of agar. The agar is allowed to solidify.

Six ml of innoculated agar is added to the solid sterile agar surface and spread evenly across the plate. It is allowed to solidify. The treated swab tips are then placed in the innoculated agar surface. They are pressed slightly to make good surface contact. The petri dishes are then fitted with either unglazed porcelain covers or covers lined with sterile filter paper. Plates are incubated in an upright position for 24 hours at 37° C.

Zones of inhibition are now determined. These are measured with a Fisher Lilly Antibiotic Zone Reader with a scale in millimeters. At least 3 measurements are performed per plate to establish distance from the edge of each petri dish to the closest microbial growth. An average of the 3 measurements are taken and reported as the Average Zone of Inhibition.

Several different classes of antimicrobial agents were measured for activity according to the aforedescribed procedures. Table I and II list the results of these experiments.

TABLE I

| SWAB BUD | REPLICATE SAMPLES | | | AVE. ZONE (mm) |
|---|---|---|---|---|
| | A | B | C | |
| 0.1% Benzathonium Chloride | 0.8, 0.7 | 0.9, 1.0 | 0.7, 0.9 | 0.83 |
| 0.1% Benzalkonium Chloride | 1.6, 1.5 | 1.7, 1.6 | 1.6, 1.5 | 1.58 |
| 0.1% Triclosan | 13.2, 12.8 | 13.0, 12.8 | 13.2, 13.4 | 13.06 |
| Untreated Control | No Zone | No Zone | No Zone | 0.0 |

*S. aureus* ATCC #6538 = positive growth

TABLE II

| SAMPLES | CONC. | S. aureus ATCC #6538 Replicate # | | | | K. pneumoniae ATCC #10031 Replicate # | | | |
|---|---|---|---|---|---|---|---|---|---|
| | | 1 | 2 | 3 | 4 | 1 | 2 | 3 | 4 |
| A | Sat. (0.1%) | 18.2, 17.9 | 17.4, 17.6 | 18.4, 17.8 | 17.9 | 13.4, 13.0 | 12.8, 12.6 | 13.4, 12.8 | 13.0 |
| B | 0.1% | 12.5, 12.7 | 12.9, 12.5 | 10.8, 11.4 | 12.1 | 9.4, 8.8 | 8.6, 8.2 | 7.8, 8.4 | 8.5 |
| C | 0.01% | 8.4, 8.9 | 8.6, 9.4 | 8.6, 8.8 | 8.8 | 5.0, 4.6 | 5.2, 5.4 | 5.4, 5.6 | 5.2 |
| D | 0.001% | 4.8, 5.0 | 5.4, 5.2 | NO ZONE | 5.1* | 2.4, 2.2 | 1.2, 1.8 | NO ZONE | 1.9* |
| E | Swab Control | 3.2, 3.4 | 3.0, 3.2 | — | 3.2* | 1.4, 1.2 | NO ZONE | — | 1.3 |

Samples: Q-Tip ® Cotton Swab Bud (Cotton Head) with the following treatments:
A Saturated w/0.1% Triclosan Solution
B w/12 mg (approx. 5–6 ul) of 0.1% Triclosan Solution
C w/12 mg (approx. 5–6 ul) of 0.01% Triclosan Solution
D w/12 mg (approx. 5–6 ul) of 0.001% Triclosan Solution
E Cotton Bud No Treatment
F Bleached Cotton (not in bud form) No Treatment
Test organims
*S. aureus* ATCC #6538
*K. pneumoniae* ATCC #10031

The foregoing description and drawing illustrate selected embodiments of the present invention and in light thereof various modifications will be suggested to one skilled in art all of which are within the spirit and purview of this invention.

What is claimed is:

1. A swab comprising:
    an elongate stem with first and second ends opposite one another;
    an absorbent covering surrounding each of the first and second ends; and
    an antibacterial agent dispersed within the absorbent covering, the antibacterial agent being in dried form, not being encapsulated within a resin and being in direct contact with either the elongate stem or absorbent covering.

2. The swab according to claim 1 wherein the antibacterial agent is selected from the group consisting of halogenated salicylanilides, halogenated carbanilides, halogenated bisphenols, alkylbenzoylacrylates, quaternary ammonium compounds, thiuram sulfides, dithiocarbamates, antibiotics, halogenated diphenyl ethers, halogenated anilides of thiophene carboxylic acids, and chlorohexidines.

3. The swab according to claim 1 wherein the antimicrobial agent is 2',4,4'-trichloro-2-hydroxydiphenyl ether.

4. A process for manufacturing swabs, the swabs being formed from an elongate stem with first and second ends opposite one another, an absorbent covering surrounding each of the first and second ends, the method comprising the steps of:
    preparing a liquid medium containing from 0.0001 to 50% by weight of an antibacterial agent;
    contacting the absorbent covering with the liquid medium containing the antimicrobial agent; and
    drying the absorbent covering.

5. The process according to claim 4 wherein the antimicrobial agent is selected from the group consisting of halogenated salicylanilides, halogenated carbanilides, halognated bisphenols, alkylbenzoylacrylates, quaternary ammonium compounds, thiuram sulfides, dithiocarbamates, antibiotics, halogenated diphenyl ethers, halogenated anilides of thiophene carboxylic acids, and chlorohexidines.

6. The process according to claim 4 wherein the absorbent covering prior to contact with the antimicrobial agent surrounds an end of the elongate stem.

7. The process according to claim 4 wherein the absorbent covering is contacted with the liquid medium containing the antimicrobial agent prior to the absorbent covering being placed on ends of the elongate stem.

* * * * *